United States Patent [19]

Lindel

[11] Patent Number: 5,742,664
[45] Date of Patent: Apr. 21, 1998

[54] X-RAY PATIENT ASSIST HANDLE ARRANGEMENT

[76] Inventor: Ralph Lindel, 271-30 77th Ave., New Hyde Park, N.Y. 11040

[21] Appl. No.: 697,287

[22] Filed: Aug. 26, 1996

[51] Int. Cl.[6] .................................................. H05G 1/00
[52] U.S. Cl. .......................................... 378/208; 378/177
[58] Field of Search ...................... 378/208, 177, 378/204

[56] References Cited

U.S. PATENT DOCUMENTS

| | | | |
|---|---|---|---|
| 1,442,027 | 1/1923 | Levenson . | |
| 2,353,969 | 7/1944 | Powers . | |
| 2,568,191 | 9/1951 | Grimm | 378/508 X |
| 2,646,514 | 7/1953 | Noschis | 378/177 |
| 3,150,260 | 9/1964 | Smith | 378/177 X |
| 3,160,143 | 12/1964 | Gray | 378/208 |
| 3,634,685 | 1/1972 | Orwig | 378/177 |
| 3,845,313 | 10/1974 | Nosol | 378/208 |
| 4,045,678 | 8/1977 | Rickard | 378/208 X |
| 4,845,747 | 7/1989 | Koike et al. | 378/208 |
| 5,048,541 | 9/1991 | Haneline . | |
| 5,168,514 | 12/1992 | Horton et al. | 378/208 X |

OTHER PUBLICATIONS

Advertisement for "Chest-X-Support" No date.
Advertisement for "Steady Rest" Positioning Support System No date.

*Primary Examiner*—David P. Porta
*Attorney, Agent, or Firm*—Leo Zucker

[57] ABSTRACT

An adjustable handle arrangement for helping a patient to stand steady for X-ray exposure imaging, includes a track assembly adapted to be mounted on a wall of an X-ray examination room. An assist handle mechanism includes an elongate handle height adjustment member, and a patient assist handle is fastened to the height adjustment member. A carriage mechanism is constructed and arranged to engage the track assembly for relative sliding movement along the direction of the track assembly. The carriage mechanism includes a plate for guiding the height adjustment member for sliding movement along the length of the adjustment member while supporting the adjustment member perpendicular to the track assembly. A clamping mechanism clamps the carriage mechanism together with the height adjustment member at a desired point along the track assembly. Thus, the patient assist handle can be fixed at a desired position in both horizontal and vertical directions with respect to the track assembly by the action of the clamping mechanism.

12 Claims, 3 Drawing Sheets

X-RAY PATIENT ASSIST HANDLE ARRANGEMENT

BACKGROUND OF THE INVENTION

1. Field of the Invention

The present invention relates generally to X-ray patient support apparatus, and particularly to an adjustable handle arrangement that can be fastened on an X-ray examination room wall.

2. Description of the Known Art

When obtaining a series of X-ray images of a patient, the patient must remain steady or else the images will be blurred and unreliable for purposes of making a medical diagnosis. If the patient must assume a natural orientation, e.g., standing next to an X-ray film exposure plate on the examination room wall with arms down, a healthy patient can maintain a steady stance long enough for satisfactory X-ray exposures.

If the patient must assume an awkward position for a particular X-ray exposure, or if the patient has a condition that prevents him or her from remaining still long enough for a desired X-ray exposure, then certain problems arise. For example, it may be painful for patients with skeletal problems or deformities to hold still for X-ray exposures, without added support. In such instances, the patient must grasp an object in the vicinity of the X-ray screen, in an attempt to gain some comfort. Because of the various physical differences and limitations among patients who must at some time be subjected to X-ray exposures, there is a genuine need for an appliance for helping such patients, whatever their physical condition or the kind of X-ray exposure needed, to hold steady long enough for clear and reliable X-rays to be taken.

U.S. Pat. No. 3,845,313 (Oct. 29, 1974) discloses apparatus for supporting a patient's arms outstretched while taking a lateral X-ray of the patients torso. The apparatus includes a base plate that is bolted to the wall of an X-ray equipment room. A generally rectangular frame has one vertical side bar pivoted in frame supports on the base plate. The frame also has several horizontal cross-bars extending between the side bar, and an opposite vertical side bar. According to the patent, the frame swings between an inactive position against the wall, and an active position in which the patient can hold one of the cross-bars while a lateral X-ray exposure is taken.

U.S. Pat. No. 5,048,541 (Sep. 17, 1991), and U.S. Pat. No. 3,160,143 (Dec. 8, 1964) disclose X-ray patient support straps or belts that encircle a patient's body. U.S. Pat. No. 2,353,969 (Jul. 18, 1944) and U.S. Pat. No. 1,442,027 (Jan. 9, 1923) show a pedestal and a chair for supporting an X-ray patient during exposure.

SUMMARY OF THE INVENTION

An object of the invention is to prevent patients from moving while taking X-rays exposures, thus improving the quality of the resulting X-ray images.

Another object of the invention is to assist patients who are in pain while standing, by providing an adjustable handle for the patient to hold comfortably while taking X-rays.

Another object of the invention is to provide a patient assist handle arrangement that can accommodate patients of various physical characteristics, and which enables them to hold still comfortably for as long as needed to take X-ray exposures.

A further object of the invention is to provide a patient assist handle arrangement that obviates the need for several cross-bars at different positions.

Another object of the invention is to provide an arrangement in which a patient assist handle can be adjusted to a desired position relative to an X-ray exposure plate, for maximum patient comfort and convenience.

According to the invention, a handle arrangement for assisting a patient includes a track assembly adapted to be mounted on a wall surface, a handle mechanism including an elongate height adjustment member, and a patient assist handle fastened to the height adjustment member. Carriage means is constructed and arranged to engage the track assembly for relative sliding movement, and to engage the height adjustment member at a selected point along the length of the adjustment member. Clamping means serves to fix the carriage means together with the height adjustment member at a desired point along the track assembly. Accordingly, the patient assist handle is set at a desired position in both horizontal and vertical directions with respect to the track assembly by operation of the clamping means.

For a better understanding of the present invention, together with other and further objects, reference is made to the following description taken in conjunction with the accompanying drawing, and the scope of the invention will be pointed out in the appended claims.

DETAILED DESCRIPTION OF THE INVENTION

Figure 1:
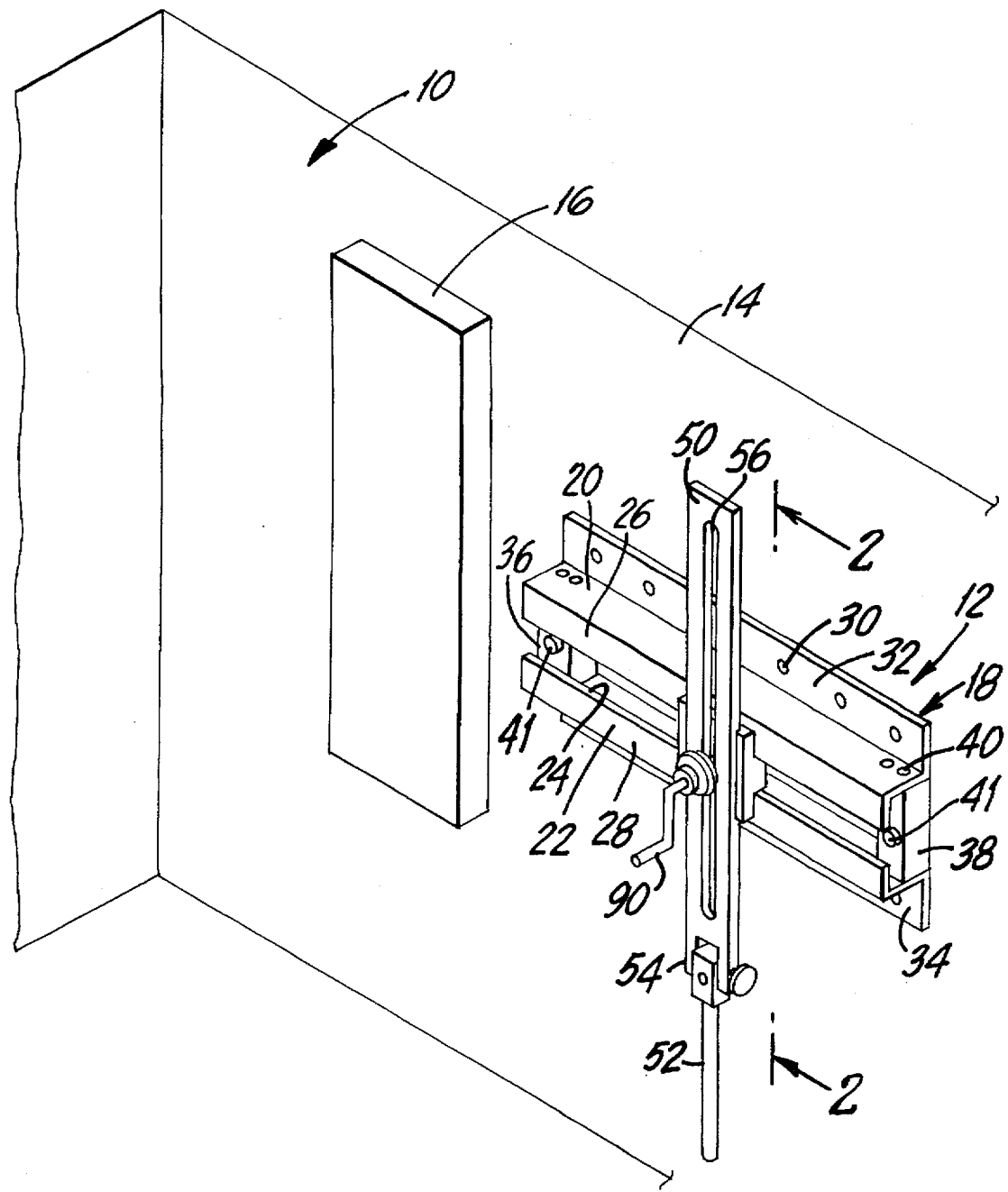
FIG. 1 is a perspective view of a medical X-ray examination room equipped with a handle arrangement according to the invention.

FIG. 1 is a perspective view of a medical examination room 10 equipped with a patient assist handle arrangement 12, according to the invention. The room 10 has a wall 14 on which an X-ray film plate holder or "bucky" 16 is mounted.

The handle arrangement 12 is mounted at one side of the film plate holder 16. As explained further below, the handle arrangement 12 may be located on the other side of the film plate holder 16 to provide additional user convenience.

Figure 2:
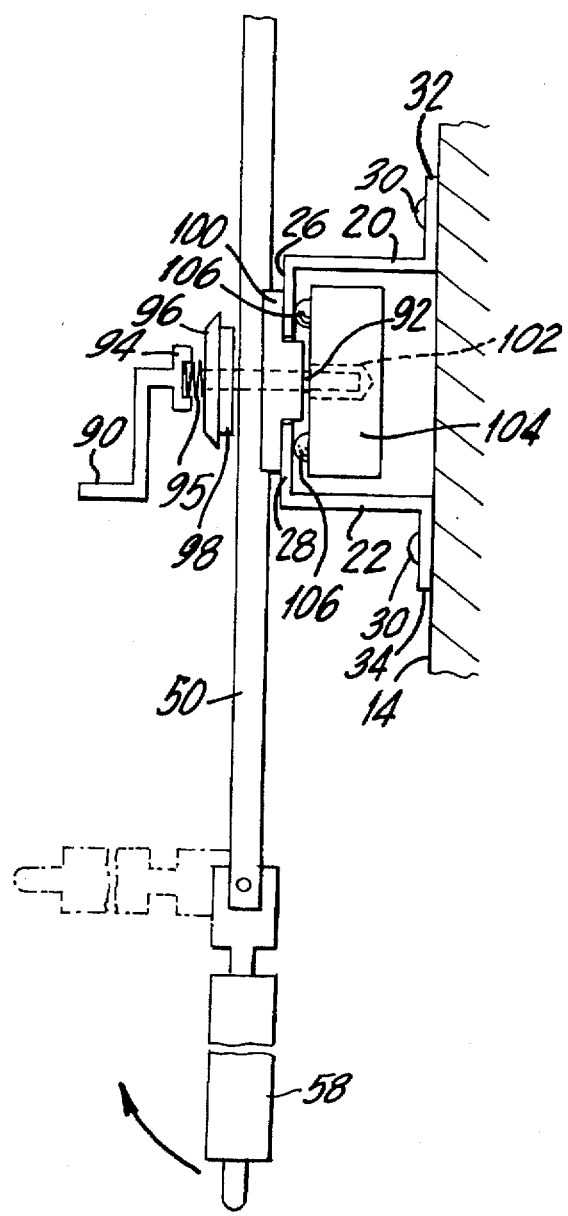
FIG. 2 is an enlarged, side view of the handle arrangement in FIG. 1, taken along section line 2—2 in FIG. 1.

Patient assist handle arrangement 12 comprises a track assembly 18 that is adapted to be fastened on the wall 14 of the examination room 10. As shown in FIGS. 1 and 2, the track assembly 18 comprises an upper "Z" channel member 20 and a lower "Z" channel member 22. Both of the channel members 20, 22 measure typically about 28-inches long, and are mounted parallel to one another in confronting relation such as to leave about a 3¼-inch wide gap 24 between confronting edges of front channel member flanges 26, 28. The channel members 20, 22 are mounted on the wall 14 via mounting screws 30, which pass through regularly spaced openings in rear flanges 32, 34 of the "Z" channel members 20, 22.

A pair of stop blocks 36, 38 are fixed one at each end of the channel members 20, 22, via screws 40 that pass through openings at opposite ends of the channel members. Set screws 41 are provided in threaded openings in the stop blocks 36, 38, wherein the heads of set screws 41 serve to limit horizontal movement of the handle arrangement as explained below. The channel members 20, 22 and the stop blocks 36, 38 can be formed of any strong, rigid material, preferably aluminum. The set screws 41 are preferably removable for reasons discussed further below.

The handle arrangement 12 also includes an elongate, handle height adjustment member 50. A patient assist bar handle 52 is fastened in the region of a lower end 54 of the adjustment member 50. The adjustment member 50 is in the form of a generally flat bar having an elongate slot 56 that is symmetric with the long axis of the member 50. A typical length for the slot 56 is 18 inches. Both of the adjustment member 50 and the bar handle 52 may be made of, e.g., aluminum or any other sturdy, light-weight material suitable for use in a medical examination room environment. The height adjustment member 50 has an overall length of typically about 24-inches, and the bar handle 52 is typically about 23-inches in length. The bar handle 52 may have a rubber or equivalent cushion sleeve 58 (see FIG.2) for providing a comfortable grip while a patient holds onto the handle 52.

Figure 4:
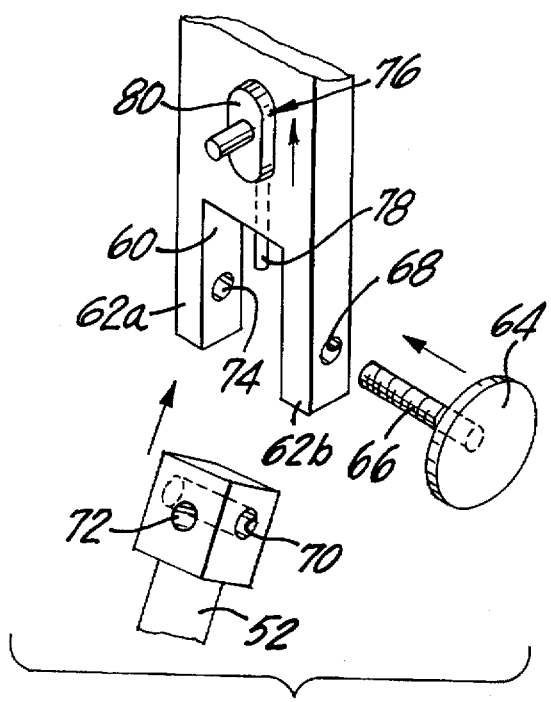
FIG. 4 is an enlarged view showing details of an adjustable joint between a handle and a height adjustment member in the arrangement of FIGS. 1 and 2.

The bar handle 52 is fastened to the height adjustment member 50 by a pivot joint for relative swinging movement. Details of the pivot joint between the bar handle 52 and its height adjustment member 50, and a pivot locking mechanism, are shown in FIG. 4.

The lower end 54 of the height adjustment member 50 has a pair of side legs 62a, 62b that define a cutout region 60. A knob 64 has a threaded shaft 66, and side leg 62b has an opening 68 through which the shaft 66 can pass. An upper end of the bar handle 52 has a cross-bore 70 that extends through the handle 52 perpendicular to the axis of the handle. The upper end of the handle 52 also has a cylindrical lock pin recess 72 in the outer periphery of the handle, and the axis of the recess 72 is perpendicular to the axis of the cross-bore 70.

The side leg 62a of the support member 50 has a threaded opening 74, and the shaft 66 of the knob 64 engages the opening 74 when the upper end of the bar handle 52 is placed in the cutout 60, and the knob shaft 66 passes through the opening 68 in leg 62b and through the cross-bore 70 in the handle 52. Clearances between the support member legs 62a, 62b and the upper end of the handle 52 are such that handle 52 can be secured or "locked" at a desired angular position with respect to the height adjustment member 50, by tightening knob 64 to cause the legs 62a, 62b to squeeze against adjacent sides of the handle 52.

A conventional lock pin mechanism 76 including a spring-loaded cylindrical lock pin 78, may be associated with the lower end 54 of the height adjustment member, wherein the lock pin 78 is retracted by urging a slide button 80 upward, while the handle 52 is swung until the lock pin recess 72 is aligned beneath the lock pin 78. At this position, the bar handle 52 is at a 90-degree angle with respect to the height adjustment member 50 (see FIG. 2). When the slide button 80 is released, the lock pin 78 is urged to enter the recess 72 in the handle, which action locks the handle at the 90-degree position.

Figure 5:
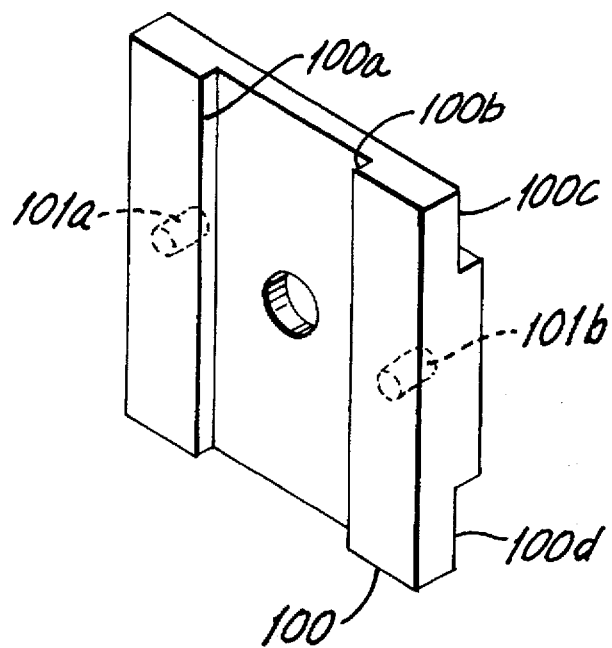
FIG. 5 is a perspective view of a guide plate in FIG. 2.

The handle arrangement 12 also includes a hand crank 90 having a threaded crank shaft 92 (see FIG. 2). The crank 90 has an annular radial flange 94 near its handle end, coaxial with the shaft 92. A coil spacer spring 95 is positioned on the shaft 92 between flange 94 and one side of a metal (e.g., aluminum) washer 96. A plastics washer 98 is positioned flush with the other side of metal washer 96. The crank shaft 92 next passes through the slot 56 in the handle height adjustment member 50, and a rectangular plastics plate 100 (FIG. 5) is placed flush against the side of member 50 that faces the wall 14. The plastics plate 100 has a central rectangular recess region on the side facing the member 50, so that the member 50 is guided by recess walls 100a, 100b, for relative sliding movement in the long direction of the member 50, i.e., vertical sliding movement as shown in FIGS. 1 and 2, and perpendicular to the direction of the track assembly 18. The side of the plate 100 facing the track assembly 18 has upper and lower rectangular recess regions 100c, 100d (FIG. 5), such that the plate 100 is guided by the channel member front flanges 26, 28 for relative sliding movement in the direction of the track assembly 18. As shown in FIG. 5, plate 100 has a central bore for passage of the hand crank shaft 92, and a pair of guide pin openings 101a, 101b whose centers are aligned in the direction of track assembly 18 (horizontally).

Figure 3:
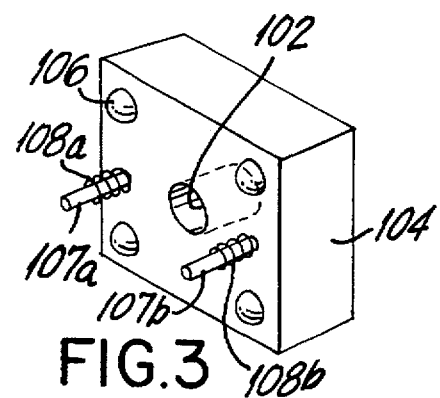
FIG. 3 is a perspective view of a carriage block in FIG. 2.

The free end of the threaded crank shaft 92 passes through the gap 24 between the edges of the front channel member flanges 26, 28, to engage a threaded opening 102 in a rigid (e.g., aluminum) carriage block 104. See FIG. 3. The block 104 is dimensioned and arranged to slide smoothly behind the front flanges 26, 28 in the direction of the channel members 20, 22 of track assembly 18. The height of block 104 as seen in FIG. 2 is slightly less than the vertical distance between the inside horizontal walls of the channel members 20, 22. The threaded opening 102 is located centrally in the block 104, and the block preferably has plastics bumpers or "feet" 106 at its four corners to slide on and clamp against the front flanges 26, 28 from behind. A pair of guide pins 107a, 107b with surrounding spacer springs 108a, 108b, project from the same side of the block 104 as the feet 106, to pass through the channel member gap 24, and are received in the guide pin openings 101a, 101b of the plastics plate 100.

When hand crank 90 is tightened, its threaded shaft 92 pulls the block 104 forward so that the block feet 106 clamp against the flanges 26, 28. Thus, the height adjustment member 50 is sandwiched between the plastics washer 98 and the plastics plate 100. When the hand crank 90 is loosened, the adjustment member 50 is guided by the plate 100 to slide in a direction perpendicular to the track assembly 18, i.e., vertically, so the bar handle 52 can be positioned a desired height above the floor of the examination room 10. Also, with the hand crank 90 loose, the crank 90 together with the height adjustment member 50 and the block 104 can be moved along the direction of the track assembly 18 (i.e., horizontally) so the patient assist bar handle 52 can be brought to a desired horizontal position with respect to the X-ray film plate holder 16 on the examination room wall 14. The height adjustment member 50 is prevented from rotating about the handle crank shaft 92, because member 50 is seated within the recess walls 100a, 100b on the front of the plate 100, and the back of the plate 100 is seated via recess regions 100c, 100d between the channel member flanges 26, 28.

In use, the bar handle 52 is swung upward from a rest position in line with the height adjustment member 50, to a horizontal position perpendicular to the examination room wall 14, at which the lock pin 78 engages the handle recess 72. The knob 64 is then tightened to lock the handle securely.

The hand crank 90 is then loosened, and the height adjustment member 50 is raised or lowered and moved left or right relative to the X-ray film plate holder 16 on the wall 14, to adjust for different patient heights, arm lengths, and stances. When the handle 52 is at a position where the patient can grasp the handle comfortably while maintaining the required stance in front of the film plate holder 16, the hand crank 90 is tightened, and the handle 52 will stay fixed at the optimum position for the patient.

In another embodiment, two track assemblies 18 may be provided, one on either side of the X-ray film plate holder 16, or a single track assembly may extend behind and on both sides of the film plate holder 16. The height adjustment member 50 together with the assist handle 52, crank handle 90, plastics plate 100 and carriage block 104 can be removed from one end of the track assembly 18, by removing the set screw 41 in the stop block 36 or 38 at the end of the track assembly 18. The height adjustment member 50, assist handle 52, and the other mentioned parts are together slid off of the channel members 20, 22, and placed together on an opposite end of the track assembly from which the set screw 41 for the corresponding stop block is removed. After the changeover, the set screws 41 are replaced in their stop blocks.

While the foregoing description represents a preferred embodiment of the invention, it will be obvious to those skilled in the art that various changes and modifications may be made, without departing from the true spirit and scope of the invention which is defined by the following claims.

What I claim is:

1. An adjustable handle arrangement for helping a patient to stand steady for X-ray exposure imaging, comprising:

an elongate track assembly adapted to be mounted on a wall of an X-ray examination room;

an assist handle mechanism including an elongate handle height adjustment member, and a patient assist handle fastened to the height adjustment member, carriage means constructed and arranged to engage the track assembly for relative sliding movement along the direction of the track assembly, the carriage means including means for guiding the height adjustment member for sliding movement along the length of the adjustment member, and means for clamping the carriage means together with the height adjustment member at a desired point along the track assembly;

wherein the patient assist handle is set at a desired position in both horizontal and vertical directions with respect to the track assembly by operation of the clamping means.

2. An adjustable handle arrangement according to claim 1, wherein said patient assist handle is in the form of an elongate bar and is pivoted to an end of said height adjustment member for adjustable swinging movement between a rest position at which the handle is aligned with said height adjustment member, and a patient assist position at which the handle is substantially perpendicular to the adjustment member.

3. An adjustable handle arrangement according to claim 1, wherein said track assembly comprises a pair of channel members adapted to be mounted parallel to one another in confronting relation on the examination room wall.

4. An adjustable handle arrangement according to claim 1, wherein said track assembly includes removable stop means at the ends of the track assembly for enabling said carriage means to be removed from one end of the track assembly, and to be placed in operative relation at another end of the track assembly by removing and replacing said stop means.

5. An adjustable handle arrangement according to claim 2, including releasable lock means associated with the handle height adjustment member, for locking the patient assist handle at said patient assist position.

6. An adjustable handle arrangement according to claim 3, wherein each of said channel members has a front flange, and said clamping means includes a block dimensioned and arranged to slide behind the front flanges of the channel members.

7. An adjustable handle arrangement according to claim 6, wherein said clamping means includes hand crank means for urging said block to clamp said height adjustment member with respect to the track assembly.

8. An adjustable handle arrangement according to claim 7, wherein said hand crank means comprises a hand crank having a crank shaft, and said height adjustment member is in the form of a generally flat bar having an elongate slot through which the crank shaft passes.

9. An adjustable handle arrangement according to claim 8, wherein the block of said clamping means has an opening for engaging said crank shaft.

10. An adjustable handle arrangement according to claim 8, wherein the guiding means of said carriage means comprises a plate member having a rectangular recess dimensioned to seat the height adjustment member, so that walls of said recess guide said height adjustment member for sliding movement in a direction perpendicular to said track assembly.

11. An adjustable handle arrangement according to claim 10, wherein the block of said clamping means has guide pins projecting toward said plate member, and said plate member has a corresponding number of openings for receiving the guide pins of said block.

12. An adjustable handle arrangement according to claim 10, wherein said plate member has recess means on a side of the plate member opposite the height adjustment member, for seating the plate member between the front flanges of the channel members of said track assembly.

* * * * *